United States Patent
Bissell et al.

(10) Patent No.: US 6,982,151 B1
(45) Date of Patent: Jan. 3, 2006

(54) DESIGN OF NOVEL ASSAYS BASED ON THE NEWLY FOUND ROLE OF DYSTROGLYCAN AND ALPHA-DYSTROGLYCAN PROTEOLYSIS IN TUMOR CELL GROWTH

(75) Inventors: Mina J. Bissell, Berkeley, CA (US); John L. Muschler, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 566 days.

(21) Appl. No.: 09/652,493

(22) Filed: Aug. 31, 2000

Related U.S. Application Data

(60) Provisional application No. 60/151,766, filed on Aug. 31, 1999.

(51) Int. Cl.
*G01N 33/577* (2006.01)

(52) U.S. Cl. ............... 435/7.23; 435/7.8; 436/501; 436/518

(58) Field of Classification Search ............. 435/7.8, 435/4, 7.1, 7.23; 436/501, 518
See application file for complete search history.

(56) References Cited

PUBLICATIONS

Henry et al., (2001, Human Pathology, vol. 32, pp. 791–795).*
Wirth et al (Eur Urol 1993;24 Suppl 2:6–12, Abstract only).*
Tockman et al (Cancer Res., 1992, 52:2711s–2718s).*
Freshney (Culture of Animal Cells, A Manual of Basic Technique, Alan R. Liss, Inc., 1983, New York, p. 4).*
Dermer (Bio/Technology, 1994, 12:320).*
Matsumura, et al., 1997, J Biol Chem, 272(21):13904–13910.*
Matsumura et al., J Biol. Chem., 1997, 272(21) 13904–13910.*
Henry, et. al., 1998, Cell, 95:859–870.*
Durbeej, et al., 1995, J. Cell Bio., 130:79–90.*
Coico, et al., 1991, Current Protocols in Immunology, p. 2.1.2–2.1.8.*
Matsumura, et al., 1993, FEBS Letters, 334(3):281–285.*
Michael D. Henry and Kevin P. Campbell, "A Role for Dystroglycan in Basement Membrane Assembly," Cell, The Cell Press (USA), p. 859–870, (Dec. 11, 1998).
Madeleine Durbeej, Erik Larsson, et al., "Non–Muscle a–Dystroglycan Is Involved In Epithelial Development," Jnl. of Cell Biology, The Rockefeller University Press (USA), vol. 130 (No. 1), p. 79–91, (Jul. 2, 1995).
Kathleen H. Holt, Leland E. Lim, Volker Straub, et al., "Functional Rescue of the Sarcoglycan Complex in the BIO 14.6 Hamster Using s–Sarcoglycan Gene Transfer," Molecular Cell, The Cell Press (USA), p. 841–848, (May 2, 1998).

* cited by examiner

*Primary Examiner*—Jeffrey Siew
*Assistant Examiner*—Misook Yu
(74) *Attorney, Agent, or Firm*—Michelle S. Chew

(57) ABSTRACT

The invention provides method for assessing tumorigenicity of mammalian cells by assaying the proteolytic fragments of 120–130 kD alpha-dystroglycan in medium surrounding mammalian cells.

13 Claims, 3 Drawing Sheets

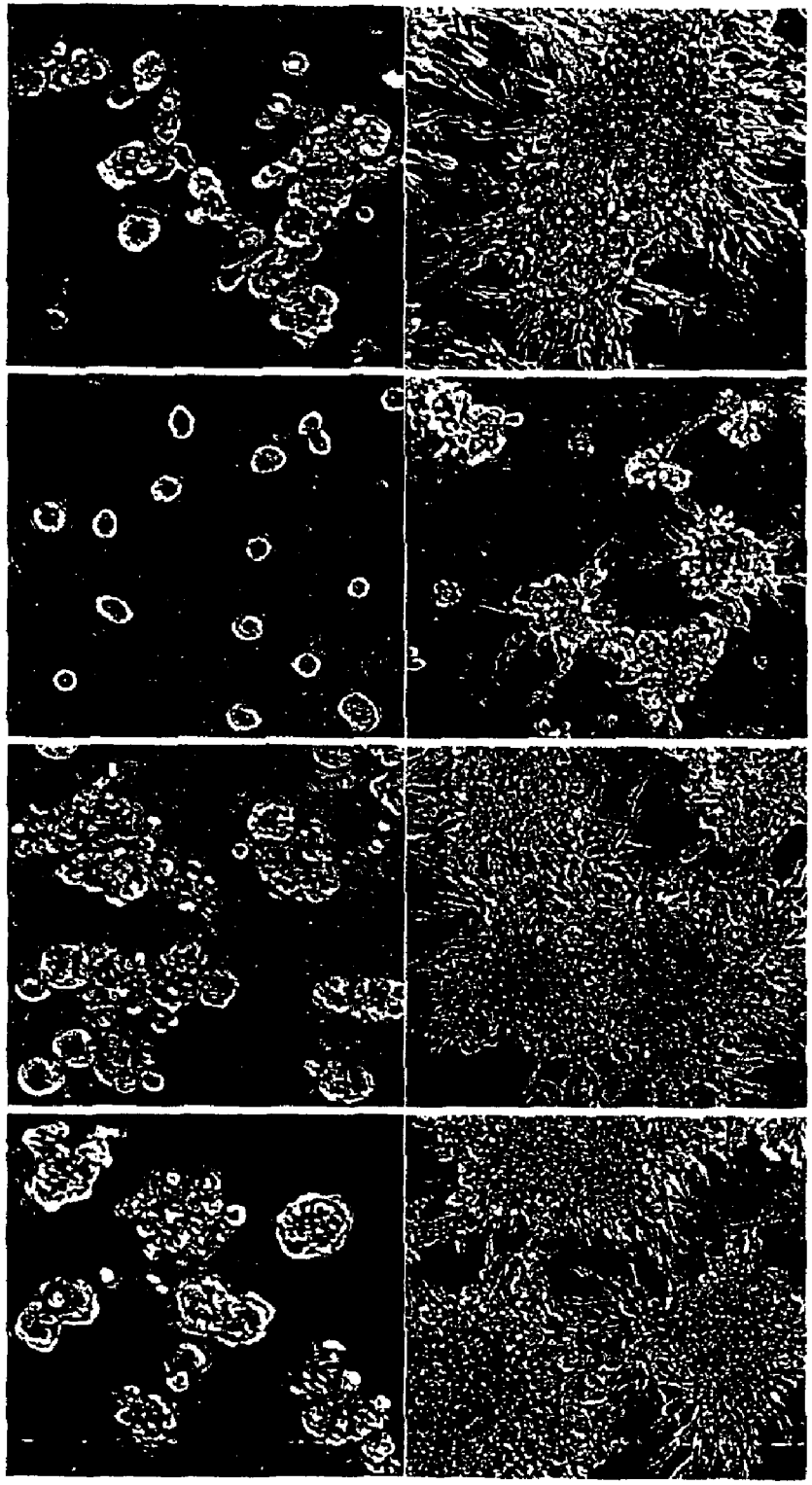

DESIGN OF NOVEL ASSAYS BASED ON THE NEWLY FOUND ROLE OF DYSTROGLYCAN AND ALPHA-DYSTROGLYCAN PROTEOLYSIS IN TUMOR CELL GROWTH

REFERENCE TO RELATED APPLICATIONS

This application claims priority benefit of U.S. provisional application No. 60/151,766, filed on Aug. 31, 1999, now abandoned, which is incorporated herein by reference.

STATEMENT REGARDING FEDERAL SPONSORSHIP

This invention was made with U.S. Government support under Contract No. DE-AC03-76SF0098 between the U.S. Department of Energy and the University of California for the operation of Lawrence Berkeley National Laboratory (LBNL). The U.S. Government may have certain rights to this invention.

BACKGROUND OF THE INVENTION

Cell growth is highly regulated in normal tissues by a variety of mechanisms in order to guide normal tissue development and homeostasis. A cell's response to the "microenvironment" is a major portion of the growth regulatory machinery. The microenvironment consists of soluble factors, adjacent cell surfaces and molecules of the extracellular matrix (ECM). Information within the microenvironment is primarily detected by cell surface receptors that bind specific molecules found in the microenvironment and elicit varied cell responses for growth, morphogenesis or differentiation.

The work reported here focuses on cell interactions with the ECM in general and a specialized form of ECM, called the basement membrane (BM). This specialized extracellular matrix serves not only as a barrier between cell layers, but also as an active signaling substrate that regulates epithelial cell growth, differentiation and tissue architecture. Key signaling components of the BM are the laminin glycoproteins. Laminin-1 alone can induce cell shape changes, growth arrest, and functional differentiation when added to cultured mammary epithelial cells (MECs). Signals from laminin are mediated by direct binding to multiple cell-surface receptors whose individual functions are not completely defined. It has been hypothesized that the aberrant behavior of tumor cells arises, in part, from alterations in cell-BM interactions. In support of this model, tumor cells frequently demonstrate altered responsiveness to BM proteins, indicating changes in BM receptor functions. Significantly, the laboratory of Dr. Mina Bissell has demonstrated that functionally normal MECs can be distinguished from tumorigenic MECs by their growth characteristics when cultured within a 3-dimensional gel of BM proteins (3D-BM assay); functionally normal MECs cultured within Matrigel will grow from single cells to form multi-cellular, polarized acinar structures that arrest growth, whereas tumorigenic MECs grow as disorganized cell masses with unregulated cell growth. The 3-D basement membrane assays distinguish between normal and tumorigenic mammary epithelial cell behavior. Normal cells growth arrest as acinar structures, whereas tumor cells do not growth arrest. This tumor cell characteristic is referred to as a "tumorigenic phenotype". This growth difference has been described in U.S. Pat. No. 5,846,536 incorporated by reference herein. Although it is evident that the cellular machinery that senses the BM is altered in tumorigenic epithelial cells, it is less certain where the critical changes occur. Studies of cell-BM interactions have largely focused on the integrins, an extensively characterized family of heterodimeric receptors. However, integrin signaling generally favors tumor cell growth and metastasis, and no integrin has been unambiguously assigned the role of tumor suppressor, leaving the possibility that other important receptors may still need to be investigated. The present invention relates to the characterization of one such receptor, dystroglycan (DG).

Accordingly, it is an object of the present invention to provide an assay of dystroglycan expression. This assay may be used to show that the laminin binding portion of α-dystroglycan is lost in tumor cells.

It is another aspect of the invention to provide an assay of dystroglycan proteolysis and shedding through the detection of cell-surface α-dystroglycan. This assay focuses on the relative ratio of α- to β-dystroglycan at the surface of cells, as compared to cells like the BT474 cells (FIG. 2, Lane 2) which shed little or no α-dystroglycan.

It is another aspect of the invention to provide an assay for the generation of dystroglycan fragments that can be used to assay for inhibitors of the metaloproteinase(s) cleaving and shedding α-dystroglycan.

It is yet another aspect of the invention to provide an assay that utilizes α-dystroglycan protein, or derivative thereof, as a substrate for a cell-free assay measuring the activity of the protease(s) cleaving it. The substrate consists of either the full-length α-dystroglycan molecule, a fragment thereof, or a synthetic peptide capable of being recognized and cleaved by the enzyme cleaving α-dystroglycan.

SUMMARY OF THE INVENTION

The present invention relates to methods and compositions for the diagnosis and treatment of cells lacking normal growth arresting characteristics. This characteristic is referred to as "tumorigenicity," which means the properties of a cell normally associated with tumor forming properties, especially, growth arresting properties, normal cell arrest, and appearance in the 3D-BM assay. Normal, non-tumorigenic cells will be polarized and, in the case of mammary epithelial cells, form acini with regulated growth properties. In the case of tumorigenic cells, the cells are disorganized and sometimes invasive, and exhibit abnormal growth.

It has been found that many tumor cells lack normal cell surface α-dystroglycan and thereby lack dystroglycan function. Re-establishment of dystroglycan function has been achieved in one cell line by transfection and over-expression of the dystroglycan gene. By re-establishing dystroglycan function, the once tumorigenic cells reverted to non-tumorigenic cells which polarized and arrested growth in the presence of basement membrane proteins, demonstrating that dystroglycan functions as a tumor suppressor. Loss of a tumor suppressor function, like that of dystroglycan, facilitates the development of tumors, therefore, cells lacking a tumor suppressor are said to have a higher "potential tumorigenicity". In some cases, loss of a single tumor suppressor, like dystroglycan, can indicate a tumorigenic state, and in other cases additional changes to the cell are required before it becomes capable of forming tumors. For the purpose of this application, either case is described as a higher potential tumorigenicity.

Most importantly, it has been found that dystroglycan can be lost from the cell surface by proteolytic shedding; some tumors cells shed a fragment of α-dystroglycan into the surrounding medium. These forms of α-dystroglycan are distinguishable because normal α-dystroglycan has a molecular weight of 180 kD, while the shed fragment has a molecular weight (Mr) of 120–130 kD (FIGS. 1A). As is known in the field, the term "Mr" refers to relative mobility on electrophoretic gels. This shedding is inhibited by the presence of metaloproteinase inhibitors (FIG. 1B and C).

The present assays may be carried out on tissue samples, the cells themselves, or on the surrounding medium. In vivo, the surrounding medium will comprise the blood and its serum.

Using the above information, one can measure the potential tumorigenicity of cells by assaying for the presence of a fragment of α-dystroglycan in medium, particularly fragments having an Mr of 120–130 kD. Identifying the presence of the α-dystroglycan fragment indicates a higher potential tumorigenicity.

Using the above information, one can also measure the potential tumorigenicity of cells by assaying to determine the ratio of the total amount of α-dystroglycan present in a cell sample relative to the amount of β-dystroglycan present in the sample. A ratio showing a deficiency of α-dystroglycan relative to β-dystroglycan indicates α-dystroglycan shedding.

A correlation between tumorigenicity and the loss of α-dystroglycan through proteolysis has been shown. Treatment of the tumorigenic cells with a metaloprotease inhibitor, at concentrations that inhibit dystroglycan shedding, reverses the tumorigenic phenotype (FIG. 3). Furthermore, treatment of cells with a genetic construct for α-dystroglycan also reverses the tumorigenic phenotype.

The present invention also provides an assay for identifying compounds which can inhibit the cleavage of α-dystroglycan by the endogenous protease that cleaves α-dystroglycan on the surface of cells. The assay comprises the steps of providing test cells, preferably tumor cells, more preferably mammary epithelial tumor cells; adding test inhibitors, along with positive and negative controls; growing the cells; and observing the resultant cell phenotype, i.e. growth arrested (normal phenotype) and tumorigenic phenotype. In cells normally having polarity, the normal phenotype will also involve polarity.

The present invention also provides an assay for identifying compounds that can inhibit the cleavage of α-dystroglycan by the creation of an in vitro assay of dystroglycan proteolysis. The assay comprises the addition of the protease, in a crude protein mixture or in pure form with a substrate. The substrate consists of either the full-length α-dystroglycan molecule, a fragment thereof, or a synthetic peptide capable of being recognized and cleaved by the enzyme cleaving α-dystroglycan.

One can also use the above information to develop an assay of proteolysed α-dystroglycan fragments in blood serum. This assay would add a labeled antibody specific for an α-dystroglycan or a fragment thereof, and assaying for the amount of bound label present in the serum. As an aspect of this assay, one would look for α-dystroglycan fragments having a Mr of approximately 120 kD).

The present invention also provides a method for suppressing the abnormal growth of tumor cells, or, in effect causing reversion of tumorigenic cells to a normal phenotype. This method involves the addition of a protease inhibitor to the cells, specifically a metaloproteinase inhibitor. The amount of inhibitor to be added can be determined by routine experimentation, in view of the examples provided herein. Metaloproteinase inhibitors may be selected from the group consisting of: TAPI, GM6001 or an pharmaceutically acceptable salt thereof or an ADAM's family protease inhibitor or pharmaceutically acceptable salts thereof Simply stated, the "effective amount" of metalloproteinase (or protease) inhibitor is reached when the cells to be treated, when grown in culture, specifically the 3D-BM culture system, show normal phenotype and growth arrest, polarity, and secondary organization, such as acini in the case of some mammary epithelial cells.

Finally, one could also use the present invention to restore normal dystroglycan function to a mammalian cell having an abnormal dystroglycan function by contacting a cell with an adenovirus transfection agent containing a normal mammalian dystroglycan gene and a cationic agent which interacts with cell surfaces or nucleic acids so as to result in a cell with said normal functioning dystroglycan gene therein.

BRIEF DESCRIPTION OF THE DRAWINGS

FIG. 1.

FIGS. 3. 3A, 3B, 3C, 3D, 3E, 3F, 3G, and 3H. 3D-BM assays of tumor cells grown in the presence of the metaloproteinase inhibitor with GM6001. (FIGS. 3A, 3B, 3C, 3D) are HMT-3522-T4 (T4) cells; (FIGS. 3E, 3F, 3G, 3H) are MDA-MD-231 cells. The cells were either untreated (FIGS. 3A and 3E), treated with 2 $\mu$M GM6001 (FIGS. 3B and 3F), treated with 40 $\mu$M GM6001 (FIGS. 3C and 3G), or treated with 40 $\mu$M C1004 (FIGS. 3D and 3H).

DETAILED DESCRIPTION OF THE PREFERRED EMBODIMENT

Dystroglycan Function

Figures 1A, 1B, 1C:
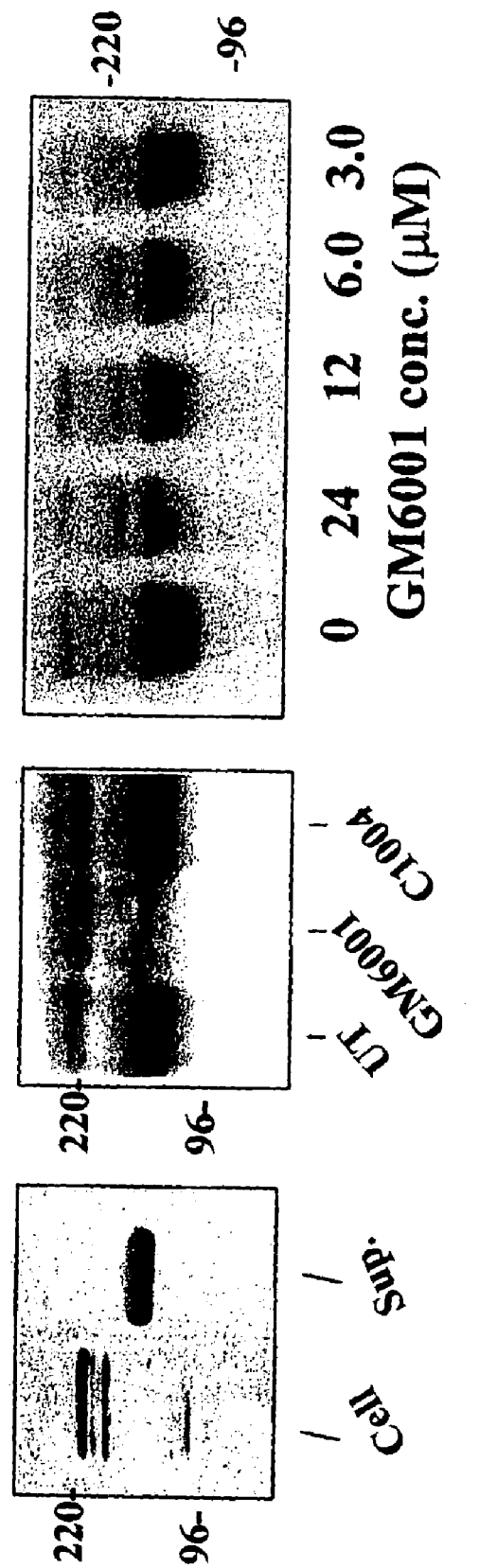
(FIG. 1A) Immuno-detection of α-dystroglycan in SCg6 mammary carcinoma cells revealing a smaller isoform in the culture supernatant (Sup.) than found on the cell surface (Cell).
(FIG. 1B) Shedding of α-dystroglycan in the supernatant is blocked by culturing with GM6001, but not in untreated (UT) cells, or in cells treated with the control agent C1004.
(FIG. 1C) Shedding of α-dystroglycan in the supernatant is differentially blocked by treatment with five different concentrations of GM6001.

Through assays of normal cell function, we have identified dystroglycan as a laminin receptor signaling cytoskeletal and cell shape changes, and cell growth arrest in normal breast epithelial cells. Dystroglycan is a known transmembrane laminin receptor composed of two non-covalently linked portions, α-dystroglycan and β-dystroglycan; see U.S. Pat. No. 5,449,616 hereby incorporated by reference. These originate from a single protein that is post-translationally cleaved. β-dystroglycan is embedded in the cell membrane. The extracellular chain, α-dystroglycan, binds to laminin. We have shown that inhibition of dystroglycan binding to laminin permits cell spreading and growth in the presence of laminin, conditions where cells would normally round-up and growth arrest. Results suggest a model whereby dystroglycan operates as a co-receptor. But, dystroglycan is shown to mediate shape changes and growth control without help from β1 and β4 integrins.

Because dystroglycan is found to regulate cell growth and cytoskeletal architecture in response to laminin in normal tissues, we have compared these signaling mechanisms in normal and malignant cells in order to ask whether dystroglycan might be altered in tumor cells. Although the β-dystroglycan protein is detected in all tumor cells, the laminin binding portion, α-dystroglycan, was found to be greatly reduced or undetectable in the majority (5 of 8). Loss of α-dystroglycan in these tumor cells was reflected by both the loss of antibody detection and loss of laminin binding ability. Therefore, within this survey α-dystroglycan was functionally absent from 5 of 8 tumor cell lines. As predicted, only those cell lines possessing adequate levels of α-dystroglycan on the cell surface were able to undergo cell rounding in response to laminin. The presence of α-dystroglycan also corresponded with the growth characteristics of tumor cells cultured within a 3D basement membrane. As described earlier, this assay has been employed to distinguish the behavior of tumor cells and normal cell in response to the BM.

Also, as described in Example 5, we have demonstrated that restoration of dystroglycan function to tumorigenic cells can revert the tumorigenic behavior of these cells, restoring normal tissue structure, differentiation potential and growth control. Re-establishment of dystroglycan function was achieved in one cell line by transfection and over-expression of the dystroglycan gene. By re-establishing dystroglycan function, the once tumorigenic cells reverted to non-tumorigenic cells which polarized and arrested growth in the presence of basement membrane proteins. Cells over-expressing the dystroglycan gene no longer form tumors after injection in nude mice. This reversion of the tumorigenic phenotype demonstrates that dystroglycan functions as a tumor suppressor.

Receptor Shedding

Because α- and β-dystroglycan are translated originally as a single polypeptide, it was surprising that α-dystroglycan was not detected on the cell surface of many cells when β-dystroglycan was present. We concluded that, by some mechanism, α-dystroglycan was being shed from the cell surface. Shedding could occur by two mechanisms: 1) simple detachment from the cell surface (because α dystroglycan is non-covalently linked), or 2) shedding induced by proteolytic cleavage of α-dystroglycan or some component attaching α-dystroglycan to the cell surface.

To test these possibilities we looked for the presence of α-dystroglycan in the culture medium of cells which shed the protein and asked if it was proteolytically cleaved. In one mammary carcinoma cell line SCg6, α-dystroglycan was detectable both on the cell surface and in the cell culture medium. Detection was achieved with an anti-α-dystroglycan antibody. One such antibody is described by Durbeej M., Campbell K. P. J. Biol. Chem. 1999; 274(37): 26609–16. Laminin binding may also be used in place of an antibody since α-dystroglycan binds specifically to laminin. However, the α-dystroglycan detected in the medium was approximately ~60 kD smaller than that on the cell surface. This suggested that α-dystroglycan was proteolytically cleaved either before or after shedding. To ask if shedding was induced by the proteolysis, we treated the cells with a general matrix metaloproteinase (MMP) inhibitor, GM6001, to see if α-dystroglycan shedding was inhibited. With cells cultured in the presence of 40 μM GM6001, the proteolysed form of dystroglycan was no longer detected in the culture medium (FIG. 1B). A control analog, C1004, had no effect at the same concentration. Therefore, loss of α-dystroglycan from the cell surface is induced by metalloprotease-induced shedding. Titration of GM6001 showed a pKi of approximately 10 μM, and a nearly complete inhibition over 25 μM (FIG. 1C). This represents an unusually high pKi for this inhibitor of metalloproteinases. Most MMPs are inhibited with pKi's of GM6001 below 1.0 μM (Galardy et al., Ann. N. Y. Acad. Sci., 1994. 732: p. 315–23). The results in FIG. 1C indicate that the protease cleaving α-dystroglycan is not among the majority of well-characterized proteases. The best candidates currently are among the ADAMs family of proteases, which are so far the only metaloproteases known to require high concentrations of GM6001 for inhibition. The ADAMs (A Disintegrin And Metalloprotease) are a recently discovered group of multidomain cell surface proteins postulated to play important roles in cell-cell and cell-matrix interactions. For example, ADAM 12 is upregulated in breast and colon cancer, and ADAM 12 supports tumor cell adhesion. Most ADAMs have no assigned substrate and the family is rapidly growing The treatment of cells with a matrix metalloprotease inhibitor can inhibit α-dystroglycan shedding and thereby increase α-dystroglycan levels at the cell surface. In turn, as previously demonstrated by gene transfection, restoration of dystroglycan function to the cell surface can restore a normal response to the BM, (i.e. organized cell structure and growth arrest).

Dystroglycan is expressed in all cells of the body, therefore, dystroglycan function and shedding is likely to play an important role in the growth and differentiation of virtually all cells. This suggests that inhibition of dystroglycan shedding may inhibit growth of any cell type, including those contacting the BM such as epithelial and endothelial cells (blood vessels). Because inhibition of endothelial cell growth is an effective therapy against tumor growth itself, an inhibitor of α-dystroglycan shedding will not only revert the tumorigenic characteristics of a tumor cell but also act against tumor growth by inhibiting angiogenesis.

Screens for Therapeutic Compounds

Recognizing that a protease sheds α-dystroglycan from the surface, this protease becomes the target for the action of therapeutic compounds to inhibit the shedding of α-dystroglycan. The use of GM6001 and TAPI to revert the tumorigenic phenotype has demonstrated proof of principle that such compounds can be therapeutic. Therefore, an assay is created for the activity of this protease using as a substrate a peptide containing the cleavage recognition sequences of this metalloprotease.

In one assay, a full-length human α-dystroglycan molecule is added to a physiological solution containing a human protease that cleaves the protein. Cleavage products are detected by separating solution components by size, e.g. through gel electrophoresis, size exclusion chromatography, etc. Test inhibitors are added to the solution and their effect on the creation of fragments by the protease are measured.

Assay for the Detection of Tissue Re-Organization and Cell Growth

We believe α-dystroglycan shedding occurs principally in cells that are reorganizing and growing. Little of such activity occurs in adult tissues, except in cases like the normal processes of mammary gland development, and perhaps angiogenesis. However, such activity would occur on a large scale during hyperplasia or tumor cell growth and the accompanying angiogenesis. α-dystroglycan is shed in two forms, one which binds laminin and a smaller portion with no known binding activity.

Any assay that detects α-dystroglycan proteolysis would be an assay for the detection of tissue re-organization and cell growth. Assays have been created to test for α-dystroglycan proteolysis in cultured cells, tissue sections, and in blood serum. Assays in cell culture include detection of shed α-dystroglycan fragments in the culture medium, and measurement of the ratio of α-dystroglycan to α-dystroglycan on the cell surface. Assays in tissue samples include detection of proteolysed α-dystroglycan fragments by immunoblotting extracted tissues or immunostaining of "nouveau antigens" created by dystroglycan proteolysis. Assays in blood serum include immunologic detection of dystroglycan fragments or nouveau antigens in serum samples.

Normal MEC Function

Using assays of normal MEC function, we divided laminin signaling functions among three different receptor systems, the β1 integrins, α6β4 integrin, and a yet to be identified "E3 laminin receptor". Most importantly, these results suggested that a non-integrin laminin receptor, binding to the E3 domain of laminin, is a critical mediator of cell morphogenesis and growth control in MECs. We now have direct evidence that the "E3 laminin receptor" is dystroglycan. First identified in muscle cells, dystroglycan is now recognized as a laminin receptor expressed in virtually all cell types, including epithelia. We have shown that overexpression of the dystroglycan gene in HMT-3522-T4 cells (T4 cells), which do not respond to laminin in morphogenesis assays, restored correct responsiveness of these cells to laminin. Moreover, these once tumorigenic cells now formed polarized, growth arrested acinar structures in 3D-BM assays, and no longer produced tumors upon injection in nude mice. The reversion of the tumorigenic phenotype of T4 cells by dystroglycan over-expression demonstrates that restoration of dystroglycan function to breast tumor cells can reduce or eliminate their tumorigenic potential, suggesting novel approaches to the treatment of cancer. The role of dystroglycan as a tumor suppressor was, until now, entirely uninvestigated.

Assays in Breast Tumor Cell Lines

Figure 2:
FIG. 2. A photograph of an immunoblot of whole cell extracts from breast tumor cell lines. Immunoblots are shown for both α-dystroglycan (top) and β-dystroglycan (bottom) present on the cell surface. Cell lines used in FIG. 2 are: 1) MCF-7, 2) BT474, 3) Skbr-3, 4) MDA-MD-468, 5) MDA-MD-231, 6) T47D, 7) MDA-MD-435, 8) MDA-MD-453.

Assays of dystroglycan expression in several breast tumor cell lines showed that the laminin binding portion of dystroglycan was lost in the majority of tumor cells. dystroglycan is composed of two subunits, α and β, which are the product of a single gene that is post-translationally cleaved. Immunoblots showed that the β-dystroglycan subunit was present in all breast tumor cell lines tested, but that the α-dystroglycan subunit, which binds laminin, was greatly diminished or absent in 5 of 8 (FIG. 2). Evidently the α-dystroglycan subunit was shed from the cell surface. Loss of α-dystroglycan in these cell lines correlated with loss of organization in the 3D BM assay and correlated with more aggressive tumor cell behavior in vivo. The ratio of α-dystroglycan to β-dystroglycan is higher in the BT474 cell line, FIG. 2, lane 2, than any other cell line or in normal cells, suggesting that some degree of shedding occurs in all cells, but that shedding is low or absent in BT474s.

In addition, we have demonstrated that shedding of α-dystroglycan can be caused by proteolysis. The α-dystroglycan molecule is detected in the supernatant of some tumor cells, but is smaller than the molecule detected at the cell surface. Shedding of cell surface molecules is most often attributed to cleavage by the ADAM subfamily of metalloproteinases (MPs). Indeed, the action of the hydroxamate MP inhibitor GM6001 implicates an ADAM; shedding of α-dystroglycan is inhibited by GM6001 at a Ki of ~10 μM (FIG. 1C). This Ki is characteristic for some ADAMs but not for other MP's which are generally inhibited by GM6001 concentrations below 30 μM. In addition, the enhanced α-dystroglycan shedding was not detected after conditioned medium from shedding cells was placed on T47D and BT474 cells, again indicating a cell surfacebound MP. Therefore, there is good evidence that α-dystroglycan is shed by the activity of an ADAM or similar MP.

The model drawn above predicts that increasing dystroglycan levels at the cell surface, through inhibition of proteolytic shedding, can revert the tumorigenic phenotype of T4 cells and inhibit the growth of other tumor cells. As shown in FIG. 3B and 3F, treatment with GM6001 at 2 μM had no effect on tumor cell growth characteristics in the 3D-BM assay, even though this concentration is sufficient to inhibit most MPs. However, GM6001 concentrations over 20 μM, (sufficient to inhibit dystroglycan shedding) reverted the T4 cells, which formed polarized and growth-arrested acini, and dramatically reduced the growth and invasion of MDA-MD-231 cells (FIGS. 3C and 3G). Our results, shown in the following Examples, perfectly match those predicted by the model discussed above.

EXAMPLES

Example 1

Assays of Dystroglycan Proteolysis through Detection of α-Dystroglycan shed from Cell Surface.

Cleavage of α-dystroglycan was detected using cultured cells that cleave and shed dystroglycan from the cell surface. Dystroglycan cleavage was assayed for by immunoblotting to detect the presence of dystroglycan fragments in the medium of cultured cells. Mammary carcinoma cell lines SCg6 or TCL1 were cultured in 10 milliliters (ml) DMEM/F12 medium supplemented with 2% fetal calf serum, 5 μg/ml insulin (Sigma Chemical Co., St. Louis, Mo.). and 50 μg/ml Gentamycin (UCSF Cell Culture Facility). The cells were allowed to grow to 80% confluence in 10 centimeter (cm) plastic tissue culture dishes. The cells were rinsed two times with phosphate-buffered saline (PBS) and the medium was then changed to 10 mls DMEM/F12 medium supplemented with insulin, and Gentamycin, but without added serum. The cells were incubated in this serum-free medium for 48 hours, then this conditioned medium was harvested and filtered through 0.4 μm filters to remove cells of cell debris. The harvested medium was consentrated from 10 ml to approximately 1.0 ml using a centriprep-30 concentrator (Amicon, Beverly, Mass.) The concentrated supernatant was added to 1/10th volume of 10× sample buffer (50% glycerol, 100 mM acetic acid, 10% SDS (w/v), 12.5% (v/v), β-mercaptoethanol, bromophenol blue) and heated at 70 degrees Celsius for 15 minutes prior to loading on SDS-polyacrylamide (SDS-PAGE) gels, and subjected to immunoblot analysis. Assays of dystroglycan cleavage and shedding in the presence of the metaloproteinase inhibitor GM6001 (AMS Scientific, Pleasent Hills, Calif.) were performed in the same manner, with varying concentrations of GM6001, or the control C104 (AMS Scientific), diluted into the serum-free culture medium at the begining of the 48 hour incubation. To compare treatments, equivalent volumes of conditioned medium from each treated cell population were loaded onto the gel to determine the relative quantities of dystroglycan shed into the medium.

After separation on an 8% SDS-PAGE gel, the proteins were electrophoretically transferred to IMMOBILON-P membranes (Millipore Corp., Bedford, Mass.) using methanol transfer buffer (20 mM Tris pH 8.3, 150 mM glycine, 0.5% SDS, 20% methanol). Following the transfer, the membranes were blocked for two hours in low salt TBST buffer (20 mM Tris-HCL, pH 8.0, 100 mM NaCl, 1.0% Tween-20 detergent) plus 5% non-fat dried milk (Lucerne). After blocking the membranes were incubated for 45 minutes with the IIH6 monoclonal antibody (primary antibody against α-dystroglycan, obtained from Dr. Kevin Campbell, University of Iowa) diluted in low salt TBST plus 5% dried milk. The primary antibody was diluted 1:20 from a concentrated (8×) stock of hybridoma supernatent. After incubation with the primary antibody, the membranes were washed with low-salt TBST and incubated 45 minutes with an horse radish peroxidase (HRP) conjugated secondary antibody (anti-IgM Product # A 8786 from Sigma). The membranes were thoroughly washed for 1 hour after the secondary antibody and the signal detected by chemiluminescence SUPERSIGNAL substrate (Pierce, Rockford, Ill.) and exposure to film. α-dystroglycan that is cleaved and shed from the cell surface appears as a distinct 130 kilodalton (kD) band in the medium (FIG. 1A), whereas α-dystroglycan isolated form the cell surface migrates as a broad 180 kD band (FIG. 1A "Cell").

Example 2

Assays of Dystroglycan Proteolysis and Shedding Through Detection of Cell-Surface α- and α-Dystroglycan Cultured cells were extracted for total protein and immunoblotted for both α- and β-dystroglycan. The ratio of α- to β-dystroglycan in each cell line measures the relative amount of α-dystroglycan retained (or lost) at the cell surface (FIG. 2). Cultured cell were extracted by completely removing the culture medium and adding RIPA extraction buffer [50 mM Tris pH 7.5, 150 mM NaCl, 1.0% NP-40, 0.5% deoxycholate, 0.1% SDS, protease inhibitor cocktail Set 1 from Calbiochem (San Diego, Calif.)] at 1.5 mls for a 10 cm culture dish. The dish containing cells and RIPA was frozen and thawed, then solubilized cells were scraped into an eppendorf tube and frozen and thawed a second time. This tube was spun in a microfuge at 13,000 rpm for 5 minutes to pellet any insoluble material, and the supernatant was transfer to a fresh tube. The protein concentration was assayed before adding 10× electrophoresis sample buffer to the extract. Following extraction the proteins were separated on an 8% SDS-PAGE gel, transferred to an immobilon-P membrane as described in Example 1. The filter was then cut along the level of 60 kD proteins. The top portion of the membrane (proteins 60 kD and larger) was immunoblotted for α-dystroglycan using the IIH6 monoclonal antibody as described in Example 1, above. The bottom portion was immunoblotted for the 43 kD β-dystroglycan molecule using the NCL-b-DG clone 8D5 monoclonal antibody (Novocastra, Newcastle upon Tyne, UK). The immunoblotting procedure for β-dystroglycan was identical to that for α-dystroglycan except the TBST contained higher salt (150 mM). The signals were detected by chemiluminescence (Pierce) and exposure to film or quantitative analysis using the ChemiImager 4000 (Alpha Inotech Corp., San Leandro, Calif.). The ratios of α- to β-dystroglycan were compared within each sample to measure the amount of α-dystroglycan lost from the cell surface. A high ratio of αto β-dystroglycan is evident in the BT474 cell line, which appears to shed little or no α-dystroglycan Example 3

Restoration or Enhancement of Dystroglycan Function in Carcinoma Cells Through Treatment with Metaloproteinase Inhibitors.

Dystroglycan function reduces the growth potential and induces polarity in normal mammary epithelial cells exposed to basement membrane proteins. As demonstrated in Example 5, restoration of dystroglycan function can induce these events in some tumor cell lines. Because dystroglycan function is lost in part by proteolytic shedding, inhibition of dystroglycan shedding can restore or enhance dystroglycan function. Therefore, restoration of dystroglycan function can be used as an assay for inhibitors of the metaloproteinase(s) cleaving and shedding α-dystroglycan. Carcinoma cell lines, including the HMT-3522-T4 cells and MDA-MD-231 cells, were cultured within the 3-dimensional basement membrane (3-D BM) assay. To accomplish this the cells were trypsinized from routine cell culture, washed once with DMEM/F12 medium, treated with soybean trypsin inhibitor, washed again with DMEM/F12 medium and resuspended in growth medium [DMEM/F12, supplemented with insulin 250 ng/ml (Boehringer Mannheim, Indianapolis, Ind.), 10 µg/ml transferrin (Sigma), 2.6 ng/ml sodium selenite (Collaborative Research), $1.4 \times 10^{-6}$ M hydrocortisone (Collaborative Research), $1 \times 10^{-10}$ M β-estradiol (Sigma), 5 µg/ml prolactin (Sigma)]. The cells were counted and 100,000 cells were resuspended in 0.3–0.5 mls of growth factor-reduced Matrigel (Collaborative Research). This mixture was placed into a 1.5 cm diameter cell culture well, and incubated at 37 degrees Celsius for 30 minutes to induce gelling of the Matrigel. Subsequently, the gelled cell-BM protein mixture was overlayed with growth medium with or without the addition of protease inhibitors or control substances. The cells were cultured at 37 degrees Celsius in a cell culture incubator at 5% carbon dioxide. The growth medium and additives were changed every two days. The additives included GM6001 at concentrations varying from 2 µM to 40 µM, TAPI (Immunex Corp., Seattle, Wash.) at concentrations from 1 to 40 µM, and an inactive control analog of GM6001 named C1004 (used at 40 µM).

GM6001 (N-[2 (R)-2 (hydroxamidocarbonylmethyl)-4-methylpentanoyl]-L-tryptophane methylamide) is a noncytotoxic synthetic inhibitor that is specific for MMPs. The hydroxamic group of GM6001 binds to the critical active site zinc atom present in MMPs. In addition, the isobutyl group and tryptophan side chain of GM6001 also binds to subsites on MMPs, which normally bind side chains of ECM proteins. Jones, P L; Crack, J., Journal of Cell Biology, 1997 Oct. 6, 139(1):279–93.

The assay was allowed to proceed from 6 to 10 days. Over this time, the cells grew from single cells within the gel to form multicellular aggregates with variable characteristics, from polarized and growth arrested (normal phenotype), to disorganized and growing (tumorigenic phenotype), to invasive. As observed in FIG. 3, GM6001 concentrations over 20 µM were required to induce polarity in HMT-3522-T4 cells and to reduce the growth potential of MDA-MD-231 cells. Measures of polarity and reduced growth potential can be easily optimized by methods existing in the art.

Beginning at 20 µM GM6001 the tumor cells regained normal cell structures and a growth arrested phenotype. Complete "reversion" of the tumor phenotype was observed at 40 µM GM6001. The reversion by GM6001 was predicted from the observed reversion by dystroglycan overexpression. In addition, the unusually high titration curve of GM6001 required for reversion in the 3D assay was also predicted by the titration of GM6001 in the α-dystroglycan shedding assay (FIG 1B). Another general MMP inhibitor, TAPI (Immunex Pharmaceuticals), was also observed to revert the T4 tumor cell line at 10 µM concentration. We conclude from these studies that the altered response of tumor cells to the basement membrane results, in part, from the proteolytic shedding of α-dystroglycan from the cell surface.

Removal of the GM6001 for 7 days (following a ten-day incubation with the inhibitor) did not permit a re-initiation of cell growth, indicating that a program of normal cell function was restored, independent of the presence of the inhibitor. This indicates that once dystroglycan function is restored to the cell, signaling from dystroglycan reinforces the message that growth arrest be maintained. It makes sense that proteolysis and shedding of α-dystroglycan is part of a cascade of events used in normal development to facilitate cell growth. Similarly, inhibition of this proteolysis could set the momentum in the opposite direction, leading to sustained reversion of the tumor phenotype.

Treatment with 40 μM GM6001 caused growth arrest, polarization and reversion to a non-tumorigenic phenotype (FIG. 3C), and potently inhibited the growth and invasion of MDA-MD-231 cells (FIG. 3G). No effect was observed with 2 μM GM6001 (FIGS. 3B and 3F) or with the control, 40 μM C1004 (FIGS. 3D and 3H).

Example 4

In vitro Assays of β-Dystroglycan Proteolysis

The α-dystroglycan protein, or derivative thereof, is used as a substrate for a cell-free assay measuring the activity of the protease(s) cleaving it. The substrate consists of either the full-length α-dystroglycan molecule, a fragment thereof, or a synthetic peptide capable of being recognized and cleaved by the enzyme cleaving α-dystroglycan. Detection of the cleavage event is assayed by any of several methods existing in the art. These methods include, but are not limited to: immunoblotting with α-dystroglycan-specific antibodies to detect proteolytic α-dystroglycan fragments; HPLC or mass spectroscopic analysis of proteolytic fragments, detection of radiolabeled fragments, detection of fluorogenic peptide cleavage. These assays can easily be modified and optimized by a variety of methods existing in the art.

The results of this assay will reveal whether, in each sample, some portion of the substrate molecule has been proteolytically cleaved into smaller fragments. Effective inhibitors of the protease will block the creation of the smaller cleavage fragments. This method will be useful for the screening, discovery, selection and optimization of protease inhibitors to be used as therapeutic agents in the treatment of tumor cell growth and other hyperplasias.

Example 5

Restoration of Dystroglycan Function Restores Normal Cell Behavior to Tumor Cells.

The tumorigenic cell line HMT-3522-T4 was found not to round-up in response to laminin when cultured on plastic, indicating that dystroglycan did not function well in these cells. In addition, this cell line is known to not to form organized acinar structures when cultured within a 3-dimensional gel of BM proteins (Matrigel), but instead displays the tumorigenic phenotype of disorganized and uncontrolled cell growth. Therefore, we over-expressed the human dystroglycan gene within these cells to see if, by restoring dystroglycan function, we could restore normal cell behavior to the tumorigenic T4 cells. Identical cells were also infected with and empty virus control (LXSN). We observed that the cells over-expressing the human dystroglycan gene respond to laminin in the medium by aggregating and rounding, whereas the control cells and rabbit dystroglycan expressing cells responds less. Placing these cells in the 3-D assay show that the T4 cells expressing the human dystroglycan gene no longer display the tumorigenic phenotype, but instead arrest growth and form organized acinar structures. Phase photographs of cultures showed the clear difference in colony size and organization; acinar-like structures were formed by cells over-expressing the disstroglycan cDNA, disorganized the srucrure are formed by the control population. a6 integrin staining showed the population of a6 integrins in dystroglycan over-expressing cells and the lack of polarity in the control population. In addition to reverting the tumorigenic phenotype in culture assays, the cells possessing restored dystroglycan function did not produce tumors after subcutane us injection in to the flanks of nude mice ($5 \times 10^6$ cells/injection), whereas the control cells did. These results reveal the role of dystroglycan as an important suppressor of tumorigenicity in cells. These results also demonstrate that restoration of dystroglycan to tumor cells is a novel therapeutic approach to slow or reverse the progression of cancer.

We claim:

1. A method for assaying mammalian cells to determine if tumor cells are present, comprising:
   a. providing a sample of medium surrounding said mammalian cells, and
   b. detecting the presence of a 120–130 kD fragment of α-dystroglycan in the medium, whereby the presence of the fragment indicates that tumor cells are present.

2. The method of claim 1, wherein said detecting comprises:
   a. adding to said sample a material selected from the group consisting of a monoclonal antibody to α-dystroglycan, and
   b. measuring the size of the α-dystroglycan fragment is 120–130 kD.

3. The method of claim 1, wherein said mammalian cells are human mammary epithelial cells.

4. The method of claim 1, wherein said medium is blood serum.

5. A method for measuring tumorigenicity of cells, comprising:
   a. providing a sample of said cells,
   b. detecting the presence of α-dystroglycan on the surface of said cells,
   c. providing a normal value for α-dystroglycan expression levels on cell surfaces; and
   d. comparing the detection levels of α-dystroglycan to said normal value, whereby a decrease in levels of α-dystroglycan on said cells of the sample indicates a higher potential for tumorigenicity.

6. The method of claim 5, wherein said detecting comprises:
   a. adding to said sample a monoclonal antibody specific for α-dystroglycan, and
   b. measuring the amount of labeled α-dystroglycan detected.

7. The method of claim 5, wherein said cells are human mammary epithelial cells.

8. The method of claim 5, wherein the step of providing a normal value comprises measuring the amount of β-dystroglycan on the surface of said cells, wherein a relative decrease in the ratio of α-dystroglycan to β-dystroglycan indicates α-dystroglycan shedding and higher potential tumorigenicity.

9. A method of determining the likelihood that a patient has a tumor, by assaying proteolysed α-dystroglycan fragments in patient serum, said method comprising the steps of:

a. contacting a serum sample to be assayed with a labeled antibody specific for α-dystroglycan, and b. assaying the amount of bound label, whereby said α-dystoglycan bound to said labeled antibody is positively correlated with existence of a tumor in the patient.

10. The method of claim 9, wherein the α-dystroglycan is a fragment of approximately 120 kD fragment.

11. The method of claim 9, wherein the α-dystroglycan is a fragment of approximately 60 kD fragment.

12. The method of claim 9, wherein said tumor cell is an epithelial cell tumor.

13. The method of claim 12, wherein said epithelial cell tumor is a breast epithelial cell tumor.

* * * * *